United States Patent [19]

Donaldson et al.

[11] Patent Number: 4,701,541
[45] Date of Patent: Oct. 20, 1987

[54] MEDROXALOL INTERMEDIATES

[75] Inventors: Richard E. Donaldson; John F. Hoops, both of Midland, Mich.

[73] Assignee: Merrell Dow Pharmaceuticals Inc., Cincinnati, Ohio

[21] Appl. No.: 933,825

[22] Filed: Nov. 24, 1986

[51] Int. Cl.⁴ .......................................... C07D 317/54
[52] U.S. Cl. .................................... 549/440; 549/441
[58] Field of Search ......................................... 549/440

[56] References Cited

U.S. PATENT DOCUMENTS 3,883,560  5/1975  Donaldson et al. ................ 549/444

Primary Examiner—Nicky Chan
Attorney, Agent, or Firm—Stephen L. Nesbitt

[57] ABSTRACT

The compounds 1-(3,4-methylenedioxyphenyl)-3-(N-benzylamino)butane and methyl 5-[[4-(3,4-methylenedioxyphenyl)-N-benzyl-2-butylamino]acetyl]salicylate are intermediates in the preparation of medroxalol.

2 Claims, No Drawings

MEDROXALOL INTERMEDIATES

FIELD OF THE INVENTION

This invention relates to new intermediates used to prepare the antihypertensive compound medroxalol.

BACKGROUND OF THE INVENTION

Medroxalol, 5-[1-hydroxy-2-[4-(3,4-methylenedioxyphenyl)-2-butylamino]ethyl]salicylamide hydrochloride having the structural formula

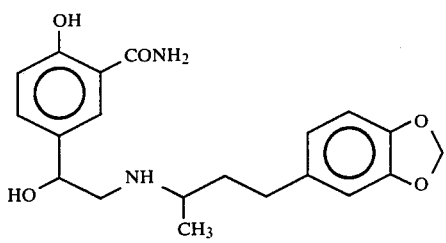

is known to possess significant antihypertensive activity. See U.S. Pat. No. 3,883,560. Although several synthetic routes to medroxalol are known, each involves at least eight individual steps. Applicants have now discovered that the compound 1-(3,4-methylenedioxypheny)-3-(N-benzylamino)butane (2, the "N-benzyl" compound) when subjected to condensation with methyl 5-(bromoacetyl)salicylate (3, the "bromoacetyl" compound) gives methyl 5-[[4-(3,4-methylenedioxyphenyl)-N-benzyl-2-butylamino]acety]salicylate (4, the "N-benzyl, methyl ester" compound) which upon hydrogenolysis and ammonolysis gives medriaxalol according to the following scheme:

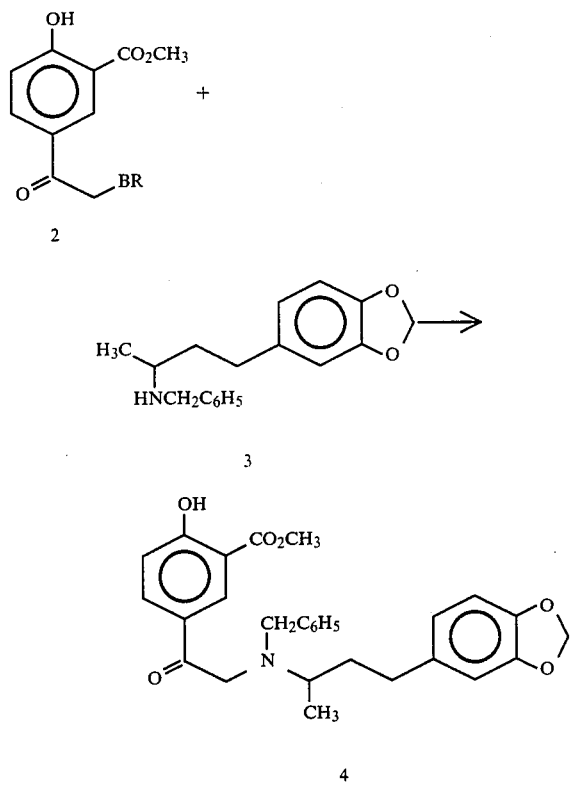

$$4 \xrightarrow{[H]} \xrightarrow{NH_3} 1$$

SUMMARY OF THE INVENTION

Medroxalol can be prepared by stepwise hydrogenolysis and ammonolysis of methyl 5-[[4-(3,4-methylenedioxyphenyl)-N-benzyl-2-butlyamino]acetyl]salicylate. This methyl salicylate intermediate can be prepared by the condensation of 1-(3,4-methylenedioxyphenyl)-3-(N-benzylamino)butane and methyl 5-(bromoacetyl)salicylate.

DETAILED DESCRIPTION

Methyl 5-[[4-(3,4-methylenedioxyphenyl)-N-benzyl-2-butylamino]acetyl]salicylate, the "N-benzyl, methyl ester" compound is converted to medroxalol by hydrogenolysis of the N-benzyl group and ammonolysis to convert the methyl ester functionality into an N-unsubstituted amide functionality. The hydrogenolysis of the N-benzyl group and concurrent reduction of the keto function is accomplished by mixing the "N-benzyl, methyl ester" compound with about 1–5 weight percent of a noble metal reduction catalyst such as 5% palladium-on-carbon using suitable solvents such as water, alcohols, for example, methanol and ethanol or mixtures The reaction vessel is pressurized with hydrogen gas to from about 2 to 20 atmospheres, preferably from about 6 to 10 atmospheres for from 4 to 20 hours, preferably about 8 hours at from 25° to 125° C., preferably at from 60° to 100° C. Isolation and purification is not necessary or desired and the intermediate can be directly carried on to the ammonolysis reaction in the same reaction vessel. To perform the ammonolysis, the reactants are cooled to below about 15° C., preferably to about 0° C. and about 10 to 1000, preferably about 100 molar equivalents of anhydrous ammonia is added to the reaction vessel which is then sealed. The reaction is allowed to proceed, preferably at about 25° C. for from 6 to 24 hours, preferably for about 14 hours. The product is isolated and purified by conventional means and preferably is converted to its hydrochloric salt, i.e., medroxalol, by any procedure known to be effective.

The compound methyl 5-[[4-(3,4-methylenedioxyphenyl-N-benzyl-2-butylamino]acetyl]salicylate (the "N-benzyl, methyl ester" compound) is prepared by the condensation of 1-(3,4-methylenedioxyphenyl)-3-(N-benzylamino)butane (the "N-benzyl" compound) with methyl 5-(bromoacetyl)salicylate (the "bromoacetyl" compound). Approximately equimolar amounts of the "N-benzyl" and "bromoacetyl" compounds are used, however a slight molar excess, for example about a 10% molar excess, of one or the other compounds, can also be advantageously used. The reaction is facilitated by the use of a base such a sodium hydroxide in an approximately equimolar quantity. A "proton sponge" such as triethylamine, pyridine or triethanolamine will also promote the progress of this reaction by removing the hydrogen bromide as it is formed. Suitable solvents may also be used. A solvent is suitable if it acts to dissolve, suspend, or disperse the reactants and does not interfere by reacting with the reagents or product. Suitable solvents include water, alcohols such as ethanol, ethers such as diethylether, dimethoxyethane, tetrahydrofuran, and acetates such as ethyl acetate and isopropyl acetate.

The temperature of the condensation reaction mixture can be any temperature at which the reaction proceeds at a convenient rate, such as from 0° to 120° C., preferably at from 25° to 65° C., and more preferably at about 50° C. The reaction is allowed to proceed for from 30 minutes to about 24 hours, preferably from 2 to 6 hours. The product, the "N-benzyl, methylester" compound, can be isolated and purified by any suitable techniques generally known by those skilled in the art. Applicants filter, then wash the reaction mixture with water and treat the organic phase with concentrated hydrochloric acid prior to isolating the product as the solid, hydrochloride salt.

The compound 1-(3,4-methylenedioxyphenyl)-3-(N-benzylamino)butane, (the "N-benzyl" compound) is prepared by the stepwise reduction of 4-(3,4-methylenedioxyphenyl)-3-buten-2-one (the "butenone" compound) and reductive alkylation of the resulting 4-(3,4-methylenedioxyphenyl)-butan-2-one (the "butanone" compound) with benzylamine according to the following scheme:

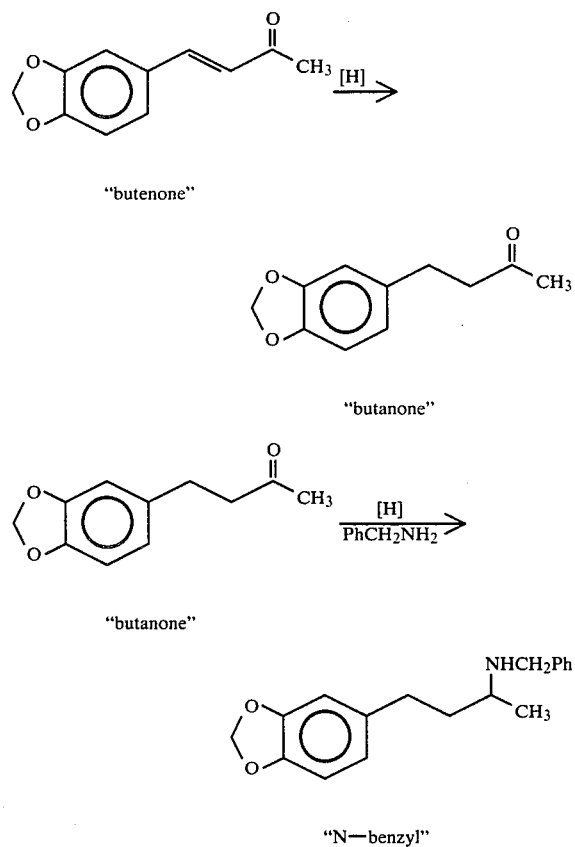

While the "butanone" compound can be isolated prior to the reductive alkylation, this is not necessary or desirable and applicants prefer to employ catalytic reductions in both steps without intervening isolation of the "butanone" compound.

Reduction of the "butenone" compound to the "butanone" compound can be accomplished with any suitable reagent which will reduce the olefinic bond in the presence of the other functionalities such as by diborane reduction or catalytic hydrogenation. Applicants have performed this reaction using 5% platinum-on-carbon catalyst under a hydrogen atmosphere. Typically a solvent such as ethanol is used. This reduction reaction is allowed to proceed for from 1 to 20 hours, depending upon the catalyst, the pressure of hydrogen, and the temperature which can be from 0° to 125° C., preferably from 25° to 100° C., more preferably about 70° to 75° C. After cooling, the hydrogen is vented and replaced with an inert atmosphere such as nitrogen gas.

The reductive alkylation is performed by reacting the "butanone" compound with a reducing agent and benzylamine. Suitable reducing agents include zinc and hydrogen chloride, sodium borohydride and hydrogen with a catalyst. With catalytic hydrogenation, a ratio of from about 0.1% to about 15% (w/w), preferably about 1% of the catalyst to butanone is employed. Typically substantially equimolar amounts of benzylamine and the "butanone" compound are used.

When catalytic reductive alkylation is used, the reaction preferably is performed without isolation of the "butanone" compound from its reaction mixture and the catalyst used to reduce the "butenone" compound to the "butanone" compound is reused. The catalytic reductive alkylation takes place with a suitable solvent, typically ethanol, and requires from 1 to about 20 hours, typically less than 10 hours, depending on the catalyst and its loading, the solvent and the temperature which can be from 0° to 110° C., preferably from 25° to 80° C., more preferably from 60° to 75° C. The "N-benzyl" compound can be purified and isolated, either as the free base or as an acid addition salt, preferably as the hydrochloride salt, by any method known to those skilled in the art. Applicants have isolated the "N-benzyl" compound from the catalytic reductive alkylation reaction mixture by filtration and subsequent atmospheric steam distillation (to remove excess benzylamine) followed by reduced-pressure distillation of the free base or by reaction with hydrogen chloride in ethylacetate to give the hydrochloride salt.

The "butenone" compound is prepared by the base catalyzed condensation of piperonal with acetone. This condensation is performed by mixing piperonal with from about 1 to about 10, preferably about 3 or 4, molar equivalents of acetone and with about 0.05 to 1, preferably about 0.1, molar equivalents of a strong base, for example a hydride such as calcium hydride, a carbonate such as potassium or sodium hydrogen carbonate, a phenoxide such as sodium phenoxide, an alkoxide such as sodium ethoxide or an hydroxide such as potassium or preferably sodium hydroxide in aqueous solution. Any suitable, non-reactive solvent which promotes the reaction can be used. Applicants have used toluene. The reaction is allowed to proceed for from 1 to 24 hours, preferably about 6 to 12 hours, depending on the solvent and the temperature which can be from 0° to 80° C., preferable about 35° to 60° C. The product, the "butenone" compound, is isolated and purified by procedures generally known in the art.

The "bromoacetyl" compound is prepared by the Friedel-Crafts acylation of methyl salicylate with acetyl chloride (or its equivalent) and subsequent bromination of the resulting methyl acetylsalicylate. The Friedel-Crafts reaction is performed by mixing the methyl salicylate with from 1 to 10 molar equivalents of the Lewis acid catalyst, preferably about 2 molar equivalents, in a suitable solvent, for example, petroleum ethers; a chlorinated hydrocarbon, such as carbon tetrachloride, 1,2-dichloroethane, methylene chloride or chloroform; a chlorinated aromatic, such as 1,2,4-trichlorobenzene or o-dichlorobenzene; carbon disulfide; or nitrobenzene.

1,2-Dichloroethane is preferred. About 1 molar equivalent to about 10 molar equivalents, preferably about 1.5 to 2 molar equivalents of acetyl chloride is added, preferably dropwise, to the mixture of methyl salicylate, Lewis acid, and solvent and the reaction is allowed to proceed for about 30 minutes to 20 hours, preferably from about 1 to 10 hours, depending on the reactants, the solvent, and the temperature which can be from about −78° to about 150° C., preferably about 0° to about 100° C., most preferably below about 35° C. The resulting methyl acetylsalicylate may be isolated from the reaction mixture by any suitable art-known procedure, such as by quenching the reaction mixture with ice water and subsequently removing the product by filtration or extraction and solvent removal. Preferably the product is not purified but is isolated in the crude by filtration and subsequent removal of the solvent from the filtrate by distillation. The crude product is used in the bromination reaction without further purification.

Lewis acid catalysts suitable for use in the Friedel-Crafts reactions described herein are, for example, a metal, such as aluminum, cerium, copper, iron, molybdenum, tungsten or zinc, a Bronstead acid, such as a phosphoric acid, sulfuric acid, sulfonic acid, or a hydrohalo acid, such as hydrochloric or hydrobromic acid; halogen substituted acetic acids, such as chloroacetic or trifluoroacetic acids; or a metallic halide, such as a boron halide, zinc chloride, zinc bromide, berryl chloride, copper chloride, iron(III) bromide, iron(III) chloride, mercury(II) chloride, mercury(I) chloride, antimony bromide, antimony chloride, titanium(IV) bromide, titanium(IV) chloride, titanium(III) chloride, aluminum bromide or preferably aluminum chloride.

The methyl acetylsalicylate is brominated by treatment with an approximately equimolar quantity of bromine in a suitable solvent. Applicants have used isopropylacetate as the solvent. The reaction is allowed to proceed for from 1 to 6 hours, typically about 1 to 2 hours at from 0° to 60° C., preferably between 20° and 35° C. The "bromoacetyl" compound can be isolated and purified in any suitable way known to those skilled in the art. Applicants have merely washed the reaction mixture with water and used the organic phase containing the "bromoacetyl" compound in the condensation step without further isolation or purification.

The compounds methyl 5-[[4-(3,4-methylenedioxyphenyl)-N-benzyl-2-butylamino]acetyl]salicylate and 1-(3,4-methylenedioxyphenyl)-3-(N-benzylamino)butane may be isolated and used in the form of their free bases or as their acid addition salts. In general, acid addition salts of these compounds are crystalline materials which are soluble in water and various hydrophilic organic solvents and which in comparison to their free base forms generally demonstrate higher melting points and an increased chemical stability. The salts are formed by reacting the free base with any suitable organic or inorganic acid. Illustrative inorganic acids which form suitable salts include hydrochloric, hydrobromic, sulphuric and phosphoric acid and acid metal salts such a sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and the sulfonic acids such as methane sulfonic acid and 2-hydroxyethane sulfonic acid. Such salts can exist in either a hydrated or a substantially anhydrous form. The hydrochloride salts are preferred.

The following examples illustrate the preparation of the novel intermediates of this invention and their use in the preparation of medroxalol.

EXAMPLE 1

The Preparation of 5-(1-hydroxy-2-(4-(3,4-methylenedioxyphenyl)-2-butylamino)ethyl)salicylamide Hydrochloride

| Materials | |
| --- | --- |
| Methyl 5-((4-(3,4-methylenedioxyphenyl)-N—(benzyl)-2-butylamino)acetyl)salicylate hydrochloride | 30.7 g (0.060 moles) |
| 5% palladium-on-carbon catalyst | 1.0 g |
| methanol | 234 g (approx) |
| nitrogen | as required |
| hydrogen | as required |
| ammonia, anhydrous | 90 g (approx) |
| ethanol | 60 g (approx) |
| 50% sodium hydroxide solution | 13.7 g |
| ethyl acetate | 120 g (approx) |
| hydrogen chloride, anhydrous | 4.8 g (0.132 moles) |
| acetic acid | 4.5 g (0.075 moles) |
| 37% hydrochloric acid | 2.6 g (0.071 moles) |

Procedure

1. The methyl 5-((4-3,4-methylenedioxyphenyl)-N-(benzyl)-2-butylamino)acetyl)salicylate hydrochloride and a slurry of the 5% palladium-on-carbon catalyst in 10 g of water are charged to a suitable reaction vessel. The mixture is placed under a nitrogen atmosphere and 151 g of methanol are added.

2. The reactor is pressurized with hydrogen to 100–200 psi and the mixture is stirred and heated at about 70° C. under 100–200 psi hydrogen for about 8 hours.

3. The mixture is cooled to about 25° C., the hydrogen vented and the mixture placed under a nitrogen atmosphere.

4. The mixture is cooled to about 0° C. and the ammonia, anhydrous, is added with stirring at a rate such that the temperature remains below 10° C.

5. The vessel is sealed and the mixture is warmed to about 25° C. for about 14 hours.

6. The ammonia is vented with warming to maintain the temperature at about 20° C. The mixture is filtered, the reactor and filter are rinsed with about 30 g of ethanol and the rinse added to the filtrate.

7. To the filtrate are added 9.6 g of 50% sodium hydroxide solution and the mixture is evaporated under vacuum to near dryness at about 50° C.

8. To the residue are added about 30 g of ethanol followed by about 80 g of ethyl acetate. The mixture is stirred and the hydrogen chloride, anhydrous, is added.

9. The mixture is cooled to about 5° C. and filtered. The cake is washed with about 20 g of cold ethyl acetate.

10. The product is dried to give approximately 28 g of solid.

11. The product and about 83 g of methanol are placed in a suitable reaction vessel.

12. The mixture is heated to about 60° C. and 4.1 g of 50% sodium hydroxide solution are added along with about 105 g of water. The mixture is heated at about 55° C. for about 1 hour.

13. The mixture is cooled to about 5° C., filtered and the cake is washed with about 9 g of water.

14. The base from step 13, 160 g of water, and 4.5 g of acetic acid plus 20 g ethylacetate are placed in a suitable reaction vessel and the mixture is stirred to dissolve the solid.

15. The mixture is clarification filtered, warmed to about 45° C., and the 37% hydrochloric acid is added.

16. The mixture is cooled to about 0° C. and filtered. The cake is washed with a small volume of cold water.

17. The product is dried at about 50° C. under vacuum. The yield of medroxalol averages 17.8 g (85% recovery).

EXAMPLE 2

The Preparation of 1-(3,4-methylenedioxyphenyl)-3-(N-benzylamino)butane Hydrochloride

| Materials | |
|---|---|
| 4-(3,4-Methylenedioxyphenyl)-3-buten-2-one | 98.4 kg (517.5 moles) |
| ethanol | 245 kg |
| nitrogen | as required |
| 5% platinum-on-carbon catalyst | 0.866 kg |
| hydrogen | as required |
| benzylamine | 51.0 kg (475.9 moles) |
| ethyl acetate | 640 kg |
| hydrogen chloride, anhydrous | 19.1 kg (523.3 moles) |

Procedure

1. A suitable reactor is charged with the 4-(3,4-methylenedioxyphenyl)-3-buten-2-one and 204 kg of ethanol. The mixture is placed under a nitrogen atmosphere.

2. A slurry of the 5% platinum-on-carbon catalyst in 3.2 kg of ethanol is charged to the reactor using 6.4 kg of ethanol as a rinse.

3. The reactor is pressurized with hydrogen to about 200 psi and heated to about 70° C. for about 7 hours.

4. The mixture is cooled to about 25° C., the hydrogen is vented, and the mixture is placed under a nitrogen atmosphere.

5. The benzylamine is charged into the reactor. The reactor is purged with hydrogen then placed under 200 psi hydrogen pressure.

6. The mixture is stirred and heated to about 70° C. and maintained at this temperature for about 7 hours (until analysis of a reaction sample indicates reaction completion).

7. The mixture is cooled to about 25° C., the hydrogen is vented, and the reaction is purged with nitrogen.

8. Filter Aid is added and the mixture is filtered. The reactor and filter cake are rinsed with about 36 kg of ethanol which is then added to the filtrate.

9. The filtrate is concentrated by removing about 180 kg of ethanol at about 40° C. under vacuum.

10. To the concentrate is added about 210 kg of water and the mixture is heated to a jacket temperature of about 130° C. to remove excess benzylamine by atmospheric steam distillation.

11. The mixture is cooled to about 30° C. and 590 kg of ethyl acetate is added followed by the hydrogen chloride.

12. The mixture is warmed to 60° C., then cooled to about 25° C. over about a 2 hour period.

13. The mixture is centrifuged and each cake load is washed with about 10 kg of cold ethyl acetate.

14. The product is dried at about 50° C. under vacuum. The yield averages 138.5 kg (83.7%).

EXAMPLE 3

The Preparation of Methyl 5-((4-(3,4-methylenedioxyohenyl)-N-benzyl-2-butylamino)acetyl)salicylate Hydrochloride

| Materials | |
|---|---|
| 1-(3,4-methylenedioxyphenyl)-3-(N-benzylamino)butane hydrochloride | 19.19 g (0.060 moles) |
| aluminum chloride | 23.59 g (0.177 moles) |
| methyl salicylate | 12.34 g (0.081 moles) |
| acetyl chloride | 9.50 g (0.121 moles) |
| 1,2-dichloroethane | 60 g |
| isopropyl acetate | 105 g (approx) |
| bromine | 12.9 g (0.081 moles, approx) |
| triethanolamine | 20.0 g (0.134 moles) |
| 37% hydrochloric acid | 5.9 g (0.060 moles) |
| 50% sodium hydroxide solution | 4.8 g (0.060 moles) |

Procedure

1. The aluminum chloride and 44.4 g of 1,2-dichloroethane are charged into a suitable reaction vessel. The mixture is stirred at about 25° C.

2. The methyl salicylate is added at a rate to maintain the temperature below 30° C. and is rinsed in with 8.0 g of 1,2-dichloroethane.

3. The mixture is stirred and the acetyl chloride is added at a rate to maintain the temperature below 35° C. and is rinsed in with 1.9 g of 1,2-dichloroethane.

4. The mixture is stirred at about 25° C. for about 3.5 hours.

5. The mixture is slowly added to about 40 g of water with stirring in a suitable reactor at a rate to maintain the temperature below 45° C. and is rinsed in with about 5.7 g of 1,2-dichloroethane. The mixture is stirred for about 1.5 hours at about 25° C.

6. The mixture is clarification filtered and an additional 19 g of water are added. After agitation, the mixture is allowed to settle and the phases are separated.

7. The 1,2-dichloroethane phase containing approximately 8.4 g of the methyl 5-acetylsalicylate is stirred and heated under vacuum to remove the majority of the 1,2-dichloroethane by distillation. Distillation is continued until the internal temperature reaches about 105° C.

8. The mixture is cooled to about 60° C. and about 88 g of isopropyl acetate are added. The mixture is cooled to about 20° C.

9. With cooling and stirring, the bromine is added over a period of about 1.5 hours at 25° C. The mixture is stirred for about 30 minutes after addition is complete.

10. About 65 g of water are added and the temperature is increased to about 35° C. After agitation, the mixture is allowed to settle and the phases are separated. The aqueous layer is removed and discarded.

11. Step 10 is repeated for a second wash.

12. To a separate reactor is added the 1-(3,4-methylenedioxyphenyl)-3-(N-benzylamino)butane hydrochloride. The sodium hydroxide solution and the triethanolamine are added and flushed into the reactor with 15 g of water. About 17 g of isopropyl acetate are then added.

13. The reaction mixture is heated to 50° C. with stirring to dissolve the solids.

14. The isopropyl acetate solution containing approximately 18.02 g of methyl 5-(bromoacetyl)salicylate from step 11 is then added to the stirred mixture at 50° C.

15. The mixture is stirred at 50° C. for four hours and then allowed to cool to ambient temperature.

16. To the cool reaction mixture is added 100 g of water to dissolve the precipitated salts. The mixture is then clarification filtered to remove some insoluble material.

17. The aqueous layer is separated and discarded.

18. The isopropyl acetate phase is treated with 37% hydrochloric acid and stirred for 6 to 12 hours.

19. The solids are collected by filtration and washed with ethyl acetate to remove color.

20. The product is then vacuum dried at 55° C. for 12 hours. The yield averages 26.3 g.

EXAMPLE 4

The preparation of 4-(3,4-methylenedioxyphenyl)-3-buten-2-one

| Materials | |
|---|---|
| piperonal | 56.7 kg (377.7 moles) |
| toluene | 130.6 kg |
| acetone | 66.2 kg (1139.4 moles) |
| 50% sodium hydroxide solution | 9.0 kg (112.5 moles) |
| ethanol | 17 kg (approx) |

Procedure

1. A suitable reaction vessel is charged with the piperonal, the toluene, the acetone, and 75 kg of water.

2. The mixture is stirred and warmed to about 45° C. and the 50% sodium hydroxide solution is added.

3. The mixture is heated at about 45° C. for about 8 hours.

4. The mixture is cooled to about 10° C. over 2 hours and stirred for an additional 30 minutes.

5. The mixture is centrifuged and washed with cold water and with a minimum volume of cold ethanol.

6. The product is dried at about 50° C. under vacuum. The yield averages 61.5 kg (85.6%).

What is claimed is:

1. A compound, 1-(3,4-methylenedioxyphenyl)-3-(N-benzylamino)butane, having the structural formula:

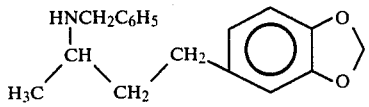

or an acid addition salt thereof.

2. The hydrochloride salt of the compound of claim 1.

* * * * *